United States Patent
Maston (10) Patent No.: US 7,033,822 B2
(45) Date of Patent: Apr. 25, 2006

(54) SELF-CONTAINED AND STREAMLINED METHANE AND/OR HIGH PURITY HYDROGEN GENERATION SYSTEM

(75) Inventor: Valerie A. Maston, Pittsfield, MA (US)

(73) Assignee: New Energy Solutions, Inc., Pittsfield, MA (US)

(*) Notice: Subject to any disclaimer, the term of this patent is extended or adjusted under 35 U.S.C. 154(b) by 51 days.

(21) Appl. No.: 10/766,552

(22) Filed: Jan. 27, 2004

(65) Prior Publication Data

US 2004/0224396 A1 Nov. 11, 2004

Related U.S. Application Data

(60) Provisional application No. 60/443,410, filed on Jan. 29, 2003.

(51) Int. Cl.
*C12M 1/00* (2006.01)

(52) U.S. Cl. .................. 435/290.1; 435/801; 210/180; 210/188; 48/61; 48/127.3

(58) Field of Classification Search .................. None
See application file for complete search history.

(56) References Cited

U.S. PATENT DOCUMENTS

| | | | |
|---|---|---|---|
| 4,409,102 A | 10/1983 | Tanner | |
| 4,696,746 A | 9/1987 | Ghosh et al. | |
| 4,784,770 A | 11/1988 | Nagao | |
| 5,108,729 A | 4/1992 | Gerhold et al. | |
| 5,215,729 A | 6/1993 | Buxbaum | |
| 5,669,960 A | 9/1997 | Couche | |
| 5,888,273 A | 3/1999 | Buxbaum | |
| 5,931,987 A | 8/1999 | Buxbaum | |
| 6,090,266 A | 7/2000 | Roychowdhury | |
| 6,168,650 B1 | 1/2001 | Buxbaum | |
| 6,183,543 B1 | 2/2001 | Buxbuam | |
| 6,241,955 B1 | 6/2001 | Alvarez, Jr. | |
| 6,299,774 B1 | 10/2001 | Ainsworth et al. | |
| 6,395,405 B1 | 5/2002 | Buxbaum | |
| 6,444,179 B1 | 9/2002 | Sederquist | |
| 6,454,944 B1 | 9/2002 | Raven | |
| 6,461,408 B1 | 10/2002 | Buxbaum | |
| 6,472,092 B1 | 10/2002 | Matsuda et al. | |
| 6,475,268 B1 | 11/2002 | Thornton | |
| 6,576,350 B1 | 6/2003 | Buxbaum | |
| 2002/0006369 A1 | 1/2002 | Buxbaum | |
| 2002/0079266 A1 | 6/2002 | Ainsworth et al. | |
| 2002/0187089 A1 | 12/2002 | Buxbaum | |

FOREIGN PATENT DOCUMENTS

WO WO 03/006387 A2 1/2003

*Primary Examiner*—David Redding
(74) *Attorney, Agent, or Firm*—Holland & Bonzagni, P.C.; Mary R. Bonzagni, Esq.

(57) ABSTRACT

A process for producing methane and/or high purity hydrogen from anaerobically decomposed organic materials as well as a methane and/or high purity hydrogen generation system that operates in accordance with this process, are provided. The inventive system, which is capable of delivering at least 40 slpm of the desired product gas or gases, is completely self-contained, requiring no outside sources of energy, and is made up of fewer components, thereby allowing for a reduced plant footprint, and a more cost-effective source of renewable methane and hydrogen.

19 Claims, 5 Drawing Sheets

SELF-CONTAINED AND STREAMLINED METHANE AND/OR HIGH PURITY HYDROGEN GENERATION SYSTEM

RELATED APPLICATION

This application claims priority from U.S. Provisional Patent Application Ser. No. 60/443,410, filed Jan. 29, 2003.

TECHNICAL FIELD OF THE INVENTION

The present invention generally relates to a process for producing methane and/or high purity hydrogen from anaerobically decomposed organic materials and further relates to a self-contained and streamlined methane and/or high purity hydrogen generation system that operates in accordance with the inventive process.

BACKGROUND ART

Steam reforming plants for hydrogen fall into two general areas depending on the type of carbon dioxide removal.

Hydrogen plants built since the late-1980s tend to use Pressure Swing Absorption (PSA) for purification, while older hydrogen plants use wet scrubbing.

The most common configuration for a wet scrubbing hydrogen plant uses two stages of shift conversion, followed by wet scrubbing and methanation. A variety of scrubbing processes are used, typically based on an amine or on potassium carbonate. Product purity depends mainly on the amount of methane leaving the reformer.

A PSA-based hydrogen plant will typically employ a steam reformer, a single high-temperature shift converter, gas cooling, and finally purification by PSA. The product purity of a PSA plant is not linked to reforming conditions as in a wet scrubbing plant. This type of plant will typically yield 99.99% purity hydrogen. To achieve higher purity hydrogen that is required for electronics, food and float glass industries (i.e., 99.9999% or higher), the PSA is either run at a lower recovery rate of less than 75% or the PSA output is run through a cryogenic system where the purity is increased.

Existing PSA-based hydrogen plants, even when designed to supply small to moderate consumers of hydrogen, are based on the same platform utilized for large hydrogen plants and are dependent upon outside sources of electrical power. Even short power outages can cause such plants to be inoperative for hours, where reformers need to be ramped back up to temperature and where PSA systems need to be brought back to full operation.

It is further noted that the hydrogen production methods outlined above depend upon fossil fuels to produce hydrogen. Reliance upon fossil fuels, however, is problematic for a number of reasons. First, fossil fuels imported from foreign sources have been the subject of exorbitant price increases and supply volume limitations. Second, the stored energy present in these fuels may be released only during combustion, which serves to release toxic pollutants into the atmosphere. It therefore appears reasonable from both an economic and environmental standpoint to develop alternative sources of fuel.

Thus, a need exists for a self-contained and streamlined hydrogen generation system that does not rely upon fossil fuels to produce hydrogen.

It is therefore an object of the present invention to provide such a system.

It is a more specific object of the present invention to provide a more reliable and cost effective system for generating renewable sources of methane and high purity hydrogen.

It is yet a more specific object to provide a self-contained methane and/or high purity hydrogen generation system that is streamlined in design and that converts organic materials such as animal waste into the desired product gas or gases.

SUMMARY

The present invention therefore provides a self-contained and streamlined process for producing methane and/or high purity hydrogen from anaerobically digested organic materials. The inventive process, which does not rely upon outside sources of energy, uses biogas to fuel one or more gas-driven devices employed therein, and basically comprises:

1) anaerobically digesting organic materials by the action of bacteria and/or enzymes contained therein to produce a biogas or mixed gas stream containing methane, carbon dioxide and trace impurities such as hydrogen sulfide, nitrogen and oxygen;
2) directing portions of the mixed gas stream to one or more gas-driven engines for fueling same, wherein the one or more gas-driven engines power a generator and optionally a compressor, and wherein the generator produces electrical energy for powering a hydrogen generation and removal system and/or a mixed gas purification device, and optionally the compressor;
3) directing remaining portions of the mixed gas stream to the compressor for compressing the gas stream; and
4) directing the compressed, mixed gas stream to:
   a. the mixed gas purification device, which serves to remove hydrogen sulfide and/or carbon dioxide from the compressed, mixed gas stream to produce a methane product stream; and/or
   b. the hydrogen generation and removal system, which comprises (a) means for generating hydrogen-rich gas from the compressed, mixed gas stream, and (b) means for selectively removing hydrogen from the hydrogen-rich gas, to produce a high purity hydrogen product stream.

The present invention further provides a self-contained and streamlined methane and/or high purity hydrogen generation system, comprising:

1) an anaerobic digester for anaerobically digesting organic materials by the action of bacteria and/or enzymes contained therein to produce a biogas or mixed gas stream containing methane, carbon dioxide and trace impurities such as hydrogen sulfide, nitrogen and oxygen;
2) at least one compressor in fluid communication with the anaerobic digester and in further fluid communication with a hydrogen generation and removal system and/or a mixed gas purification device;
3) at least one mixed gas-driven generator in fluid communication with the anaerobic digester and in electrical communication with the hydrogen generation and removal system and/or the mixed gas purification device, and optionally in further electrical communication with the compressor(s); and
4) a. the mixed gas purification device, which serves to remove hydrogen sulfide and/or carbon dioxide from the mixed gas stream to produce a methane product stream, wherein the mixed gas purification device is in fluid communication with the compressor and is in electrical communication with the generator; and/or b. the hydrogen generation and removal system, which comprises (a) means for generating a hydrogen-rich gas from the compressed, mixed gas stream, and (b) means for selectively removing hydrogen from the hydrogen-rich gas to produce a high purity hydrogen product stream, wherein the hydrogen generation and removal system is in fluid communication with the compressor and is in electrical communication with the generator.

Other features and advantages of the invention will be apparent to one of ordinary skill from the following detailed description and accompanying drawings.

Unless otherwise defined, all technical and scientific terms used herein have the same meaning as commonly understood by one of ordinary skill in the art to which this invention belongs. All publications, patent applications, patents and other references mentioned herein are incorporated by reference in their entirety. In case of conflict, the present specification, including definitions, will control. In addition, the materials, methods, and examples are illustrative only and not intended to be limiting.

BRIEF DESCRIPTION OF THE DRAWINGS

Particular features of the disclosed invention are illustrated by reference to the accompanying drawings in which.

BEST MODE OF CARRYING OUT THE INVENTION

The methane and/or high purity hydrogen generation system of the present invention is completely self-contained, requiring no outside sources of energy (e.g., electric, natural gas), and is capable of delivering at least 100 cubic feet per hour at standard conditions (100 scfh) or 40 standard liters per minute (40 slpm) of the desired product gas or gases. The inventive system requires fewer components, thereby allowing for a reduced plant footprint and a more cost-effective source of renewable methane and hydrogen. Further, the inventive system depends upon anaerobically digested organic materials and not fossil fuels to produce methane and high purity hydrogen. In a preferred embodiment, the inventive system produces higher purity hydrogen than that produced by standard hydrogen generation plants.

Figure 1:
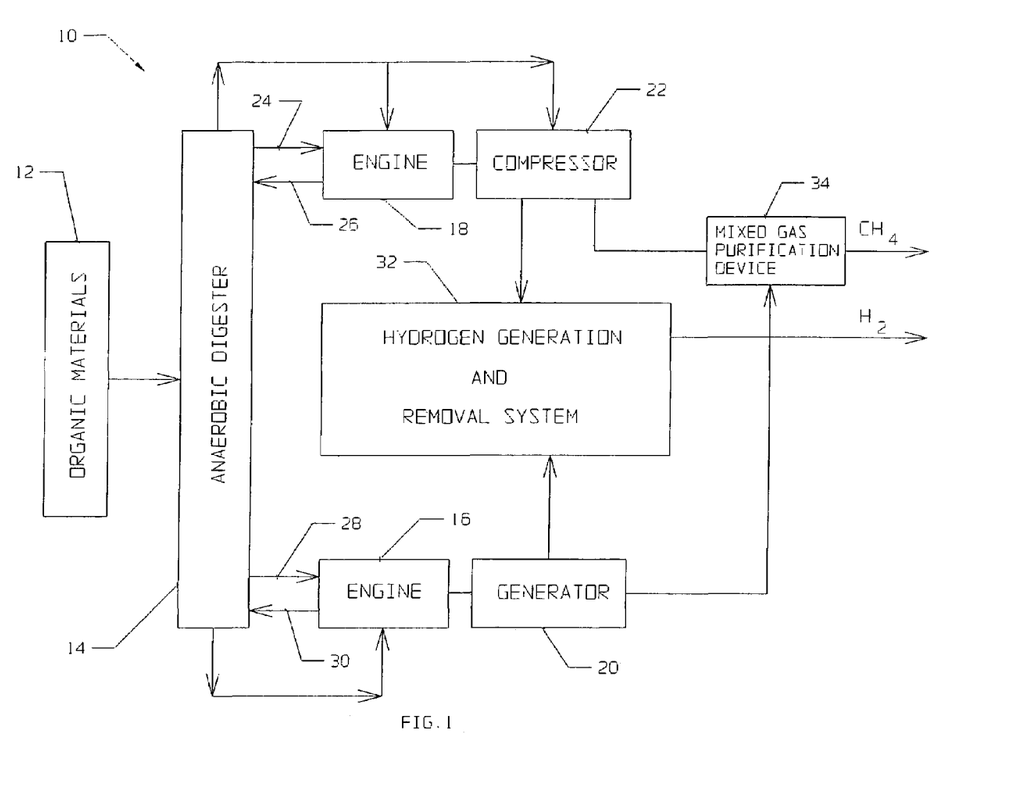
FIG. 1 is a process flow schematic of a preferred embodiment of the methane and/or high purity hydrogen generation system of the present invention.

Referring now to FIG. 1 in detail, a process flow schematic of a preferred embodiment of the methane and/or high purity hydrogen generation system of the present invention is shown and generally designated by reference numeral 10. In this embodiment, organic materials 12 such as plant material, animal waste, food waste, or human waste, are fed into anaerobic digester 14. An anaerobic microbe is added to digester 14 to form a reaction solution. The digestion period is allowed to last for from about 3 to about 21 days, while forming a biogas or mixed gas stream containing predominantly methane and carbon dioxide along with trace impurities such as hydrogen sulfide, nitrogen and oxygen. As will be readily apparent to those skilled in the art, the length of the digestion period will depend upon the type of organic materials 12 being processed and the design of the digester 14.

Portions of the biogas or mixed gas stream are passed to gas-driven engines 16, 18, which power a generator 20 and a low-pressure compressor 22, respectively.

In a more preferred embodiment, gas-driven engines 16, 18, are equipped with (1) in-line hydrogen sulfide filters, and (2) water-jacketed exhaust manifolds. The water-jacketed exhaust manifolds serve to cool exhaust gases prior to discharge through an exhaust system and to heat biogas passing through the manifolds by way of inlet lines 24, 28, and outlet lines 26, 30, thus providing heat to digester 14.

Generator 20 produces electrical energy for a hydrogen generation and removal system 32 and/or for a mixed gas purification device 34 at a particular nominal voltage and at a frequency that is constant or variable. A battery may be used in conjunction with generator 20 in order to make system 10 electrically self-sufficient.

Portions of the biogas or mixed gas stream produced in digester 14 are also passed to the low-pressure compressor 22, which compresses the gas to a pressure exceeding the operating pressure of the hydrogen generation and removal system 32, or the mixed gas purification device 34. In a preferred embodiment, the gas is compressed to a pressure of up to about 2.17 megapascals (MPa), more preferably up to about 2.86 MPa.

Upon leaving compressor 22, the compressed biogas is directed to the hydrogen generation and removal system 32 and/or to the mixed gas purification device 34.

The hydrogen generation and removal system 32 basically comprises (a) means for generating a hydrogen-rich gas from the compressed, mixed gas stream, and (b) means for selectively removing hydrogen from the hydrogen-rich gas to produce a high purity hydrogen product stream.

The hydrogen-rich gas generation means involves the use of hydrogen and hydrocarbon conversion reactions including, but not limited to, steam reforming, water-gas shift reactions, methanol synthesis and catalytic combustion. These reactions are usually carried out at temperatures between 200° C. and 1000° C. Currently these reactions are industrially run using catalyst pellets that consist of an active catalytic metal or metal oxide deposited on high surface area ceramic pellets.

In a preferred embodiment, the hydrogen-rich gas generation means involves the use of steam reforming and shift conversion processes or techniques.

During steam reforming, steam is reacted with a hydrocarbon fuel over a catalyst (typically nickel-, copper-, or noble metal-based catalysts) to form primarily hydrogen, carbon dioxide and carbon monoxide, while during shift conversion, carbon monoxide reacts with steam to produce carbon dioxide and additional hydrogen. More specifically, the following principal reactions occur in the mixed gas stream upon entering system 32:

$$CH_4 + H_2O \leftrightarrow CO + 3H_2$$

$$CO + H_2O \leftrightarrow CO_2 + H_2$$

$$CH_4 + 2H_2O \leftrightarrow CO_2 + 4H_2$$

The overall reaction noted above is highly endothermic, and is normally carried out at elevated catalyst temperatures ranging from about 650° C. to about 875° C. Such elevated temperatures are typically generated by the heat of combustion from a burner incorporated in a reforming furnace in the steam reformer.

In a more preferred embodiment, the hydrogen-rich gas generation means further involves the use of feedstock purification in which hydrogen sulfide is removed from the mixed gas stream entering system 32 to maximize the life of the downstream steam reforming and other catalysts. As is well known to those skilled in the art, hydrogen sulfide may be removed using conventional hydrogen sulfide scrubbers or absorbents such as activated charcoal, zinc oxide and mixtures thereof.

The means for selectively removing hydrogen from the hydrogen-rich gas stream to produce a high purity hydrogen product stream is not limited. The gas stream may be treated in a number of ways to achieve the required hydrogen purity. For example, $CO_2$ may be removed by means of a scrubber followed by drying and cryogenic purification. Alternatively, a pressure swing adsorption (PSA) unit, or an apparatus employing one or more gas extraction membranes for removing hydrogen from a mixed gas flow, may be used to purify the gas stream.

In a preferred embodiment, the means for selectively removing hydrogen from the hydrogen-rich gas involves the use of hydrogen-permeable membranes. More specifically, membrane reactors, which combine in one unit a reactor that generates hydrogen with a semi-permeable membrane that extracts it, are employed.

In accordance with the above, and in a more preferred embodiment, the hydrogen generation and removal system 32 comprises a steam reformer and a high temperature shift/membrane reactor (HTS/MR).

As noted above, the steam reformer serves to generate hydrogen from the compressed, mixed gas stream by way of the following reaction:

and basically comprises one or more steam boilers in fluid communication with one or more steam reforming furnaces containing a plurality of tubes filled with reforming catalysts and one or more burners. The hydrogen-rich gas stream exiting the steam reformer is cooled to a temperature of from about 370 to about 815° C. prior to entering the HTS/MR. The heat recovered from the hydrogen-rich gas stream may be used for preheating the compressed, mixed gas stream entering the steam reformer and/or for preheating the process water used to produce steam in the boiler(s).

Figure 2:
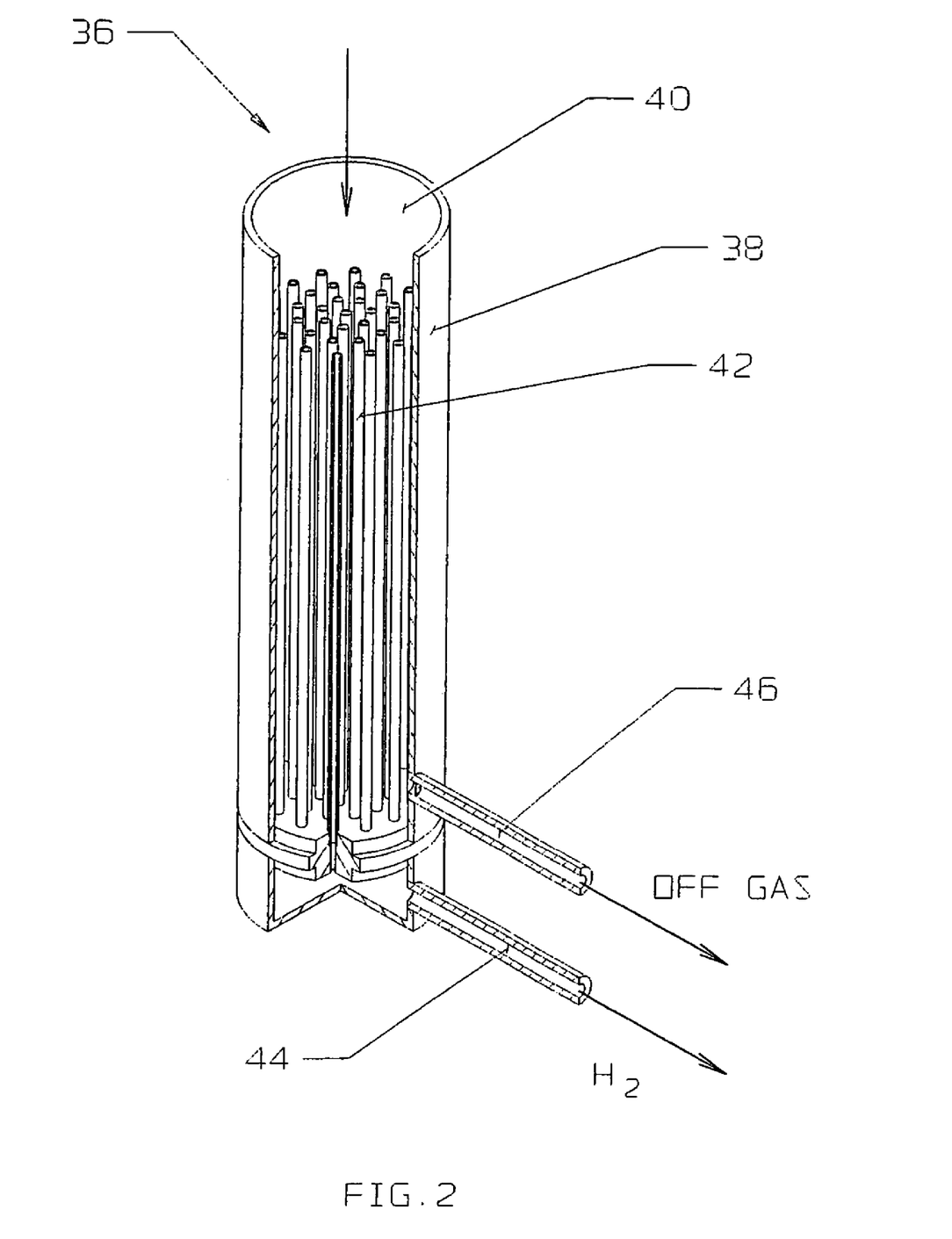
FIG. 2 is a partial cross-section of a high temperature shift/membrane reactor for generating and selectively removing hydrogen from a hydrogen-rich mixed gas stream.

The HTS/MR serves to (1) generate hydrogen from carbon monoxide produced in the steam reformer by way of the following exothermic water-gas shift reaction:

and to (2) selectively remove hydrogen from the hydrogen-enriched, mixed gas stream. In this more preferred embodiment, and as best shown in FIG. 2, the HTS/MR 36 is made up of: a chamber 38; an inlet port 40 for introducing the mixed gas stream into the chamber 38; a plurality of hydrogen gas separator membranes 42 in the form of tubes having an outer surface in fluid communication with the mixed gas stream, and an inner surface in fluid communication with the high purity hydrogen product stream that has passed through the membrane tubes 42, which are housed within the chamber 38; a catalyst located within chamber 38 (not shown) for facilitating the exothermic water-gas shift reaction; a first outlet port 44 for removing the high purity hydrogen product stream; a second outlet port 46 for removing a waste gas stream; and optionally, a cooling means (not shown) for withdrawing thermal energy from the chamber 38. Such HTS/MRs are described in U.S. Pat. No. 6,461,408 B2 to Robert E. Buxbaum, which is incorporated herein by reference.

It is noted that the membrane tubes 42, shown in FIG. 2, operate on partial pressure differences in the hydrogen. In other words, as hydrogen demand increases, the partial pressure of hydrogen on the outside of the tubes 42 would decrease, causing more hydrogen to flow across the tubes 42, while as hydrogen demand decreases, the partial pressure of hydrogen on the outside of the tubes 42 would increase, causing less hydrogen to flow across the tubes 42. In contrast, PSA systems are not as load sensitive. As the hydrogen output demand changes, the PSA bed times need to be adjusted to maintain the hydrogen purity. Typical ramp rates for PSA systems range from about 0.5 to about 2.0% per minute, while the ramp rates for the tubes 42 are instantaneous.

The process accomplished by way of the HTS/MR 36 includes reacting the mixed gas stream exothermically with a catalyst in the presence of the membrane tube(s). It is noted that steam reforming and water gas shift reactions are reversible and are limited by thermodynamic equilibrium. By including tubes 42 in the HTS/MR 36, the reactions can be brought to near completion at much higher operating temperatures.

A preferred water-gas shift catalyst is an iron oxide catalyst.

The steam reforming furnace(s) may be operated with condensed off-gas exiting the hydrogen generation and removal system 32 via outlet port 46. In addition, mixed gas from the anaerobic digester 14 may be used to start up the reforming furnace(s) and to provide additional thermal energy to the furnace(s) during operation.

The inventive system 10, when dedicated to the production of hydrogen, produces from about 40 to about 2,400 slpm of hydrogen at 99.99999% purity and at from about 100 to about 450 kilopascals (kPa). The high purity hydrogen product stream exiting the hydrogen generation and removal system 32 may be used as a low-pressure (i.e., 100 to 310 kPa) fuel for hydrogen fueled devices including fuel cells, hydrogen engines, or bearings in standard electric power plants. The low-pressure, high purity hydrogen product stream may also be used in various production processes such as fiber optic cable, semi-conductors, float gas, hydrogenation of oils, metal processing or electronics manufacturing.

The mixed gas purification device 34 for removing hydrogen sulfide and/or carbon dioxide from the mixed gas stream to produce a methane product stream is not limited. As noted above, hydrogen sulfide may be removed using conventional hydrogen sulfide scrubbers or absorbents such as activated charcoal, zinc oxide and mixtures thereof, while carbon dioxide may be removed using e.g. membrane gas separation techniques. Membrane gas separation is based on the difference in permeation rates of gas components through a selective membrane, with selected membrane materials (e.g., cellulose acetate, polysulfone and polyimide membranes and films or membranes made from fluorinated polymers) being much more permeable to hydrogen than to other gases such nitrogen, carbon dioxide and hydrogen sulfide.

The inventive system 10, when dedicated to the production of methane, produces from about 40 to about 2,400 slpm of methane at >90% purity and at from about 1.82 to about 2.86 MPa. The methane product stream exiting the mixed gas purification device 34 meets the Society of Automotive Engineers (SAE) standards for compressed natural gas (CNG) and may be used for low-pressure applications such as fuel for natural gas engines and any other devices that use pipeline natural gas.

Figure 3:
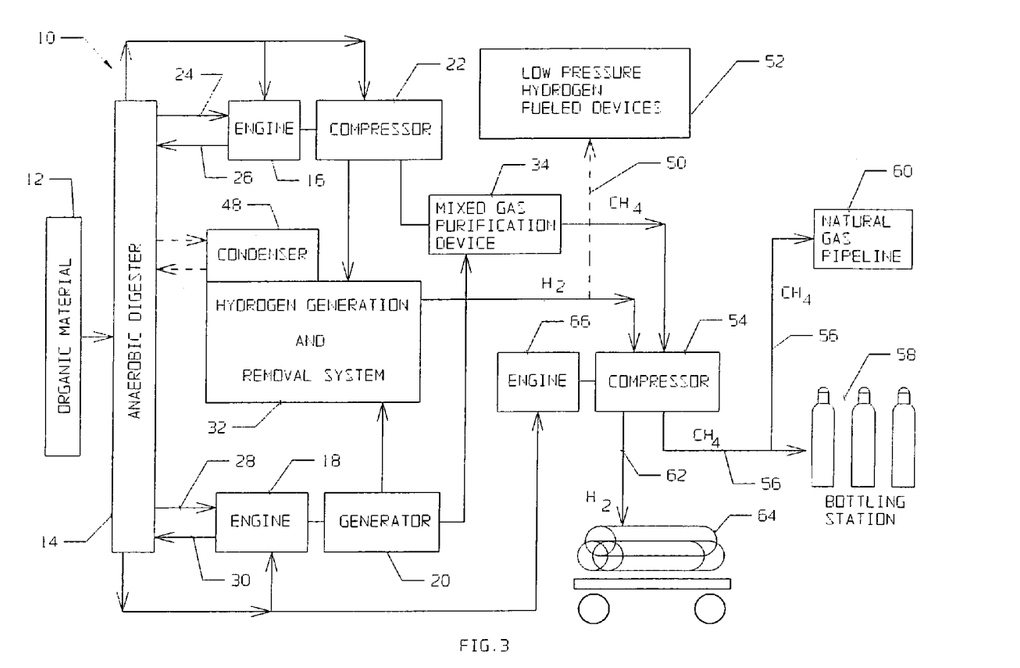
FIG. 3 is a process flow schematic of a more preferred embodiment of the methane and/or high purity hydrogen generation system of the present invention.

In yet a more preferred embodiment and as best shown in FIG. 3, the methane and/or high purity hydrogen generation system 10 of the present invention, may further comprise (1) at least one condenser 48 in fluid communication with the anaerobic digester 14 and optionally, in fluid communication with the hydrogen generation and removal system 32 (not shown) for removing at least a portion of any water contained in the gas streams produced thereby; (2) means 50 for directing the high purity hydrogen product stream to low pressure hydrogen fueled devices 52; (3) a high pressure, mixed-gas driven compressor 54 in fluid communication with the anaerobic digester 14, in further fluid communication with the hydrogen generation and removal system 32 and/or the mixed gas purification device 34, and in further fluid communication with e.g., pipelines and/or storage devices; (4) means 56 for directing a further compressed methane product stream to e.g., a bottling station 58 and/or to a natural gas pipeline 60; and (5) means 62 for directing a further compressed high purity hydrogen product stream to e.g., one or more gas cylinders and/or tube trailers 64.

Water collected in condenser 48 and in a possible second condenser in fluid communication with the hydrogen generation and removal system 32, may be added to feed water for the steam reformer boiler(s).

Compressor 54, which is powered by gas-driven engine 66, serves to further compress the gas for higher-pressure applications. In a preferred embodiment, high purity hydrogen gas is compressed to a pressure of greater than or equal to 20.8 MPa (more preferably from about 34.5 to about 69.0 MPa) and is then directed to e.g. tube trailers for storage or to a hydrogen filling station for vehicles. It is noted that in most high-purity gas manufacturing processes, it has been conventional for the gases to be stored in and supplied from standard gas cylinders. The limited storage capacity, weight and awkward nature of these gas cylinders has prompted the industry to begin to require gases to be supplied in large volume containers which need to be changed only at infrequent intervals (usually measured in months rather than hours, as with individual gas cylinders). A preferred type of large volume container is the "tube trailer," a semi-trailer which is constructed with a number of high capacity, high pressure vessels or "tubes" that are interconnected or operate through a common manifold.

Figure 4:
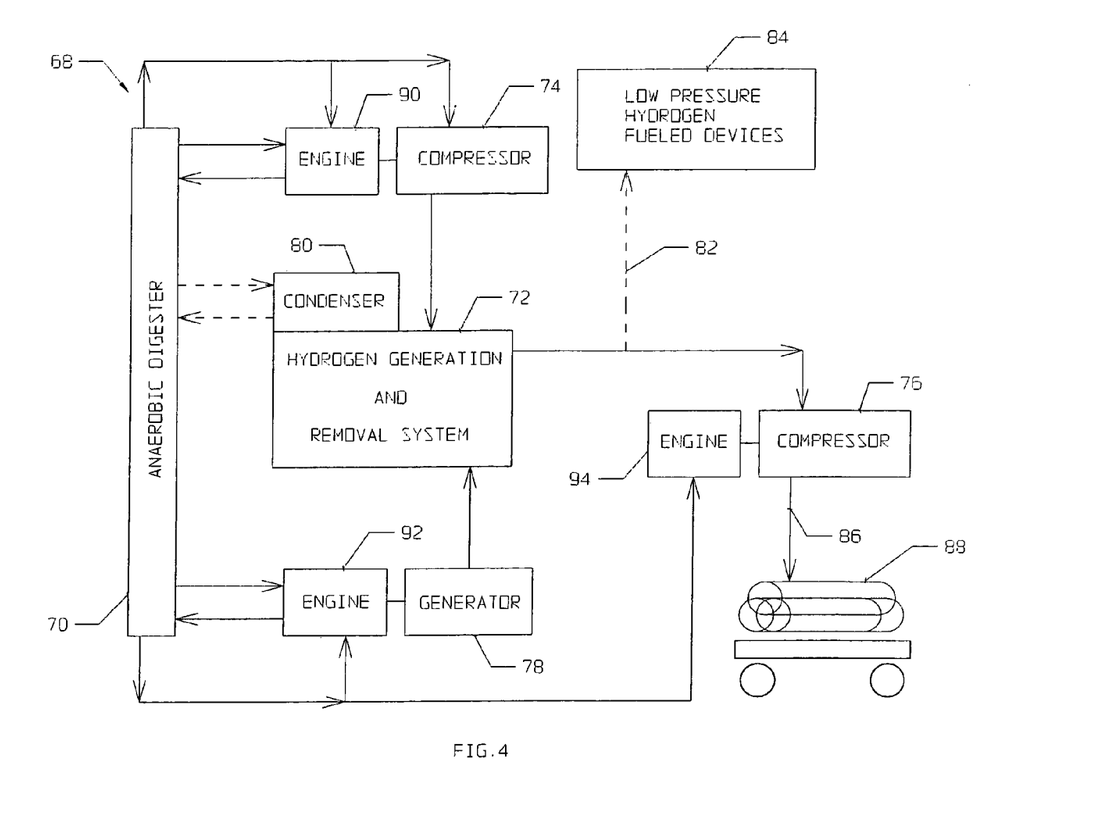
FIG. 4 is a process flow schematic of a most preferred embodiment of s the high purity hydrogen generation system of the present invention.

Referring now to FIG. 4, a first most preferred embodiment of, the present inventive system is shown and generally designated by reference numeral 68. In this first most preferred embodiment, system 68 comprises:

1) an anaerobic digester 70;
2) a hydrogen generation and removal system 72 comprising (a) a steam reformer (not shown), and (b) a high temperature shift/membrane reactor (not shown);
3) first and second mixed gas-driven compressors 74, 76, in fluid communication with the anaerobic digester 70 and in further fluid communication with the hydrogen generation and removal system 72;
4) a mixed gas-driven generator 78 in fluid communication with the anaerobic digester 70 and in electrical communication with the hydrogen generation and removal system 72;
5) optionally, a condenser 80 in fluid communication with the anaerobic digester 70 for removing at least a portion of the water contained in the mixed gas stream produced by the digester 70;
6) means 82 for directing the high purity hydrogen product stream exiting the hydrogen generation and removal system 72 to low-pressure hydrogen fueled devices 84; and
7) means 86 for directing the high purity hydrogen product stream exiting the second compressor 76 to one or more gas cylinders and/or tube trailers 88.

In operation, mixed gases from digester 70 are initially directed to gas-driven engines 90, 92, which power the first compressor 74 and the generator 78, respectively. Once the first compressor 74 and the generator 78 are operational, they are brought online. Mixed gases from the digester 70 are then supplied to the steam reformer (i.e., to one or more mixed gas-fired reforming furnaces and to one or more steam boilers), while process water is supplied to the boiler(s). Once the steam reformer is up to temperature, the hydrogen generation and removal system 72 is brought online and hydrogen begins to be produced. Mixed gases from digester 70 are then directed to gas-driven engine 94, for powering the second compressor 76. Once sufficient hydrogen flow rates (i.e., 25 to 30% of rated output) are achieved, the second compressor 76 is brought online. As noted above, low pressure hydrogen produced by system 72 may be directed to low pressure hydrogen fueled devices 84, while high pressure hydrogen may be directed to e.g., one or more gas cylinders and/or tube trailers 88.

Figure 5:
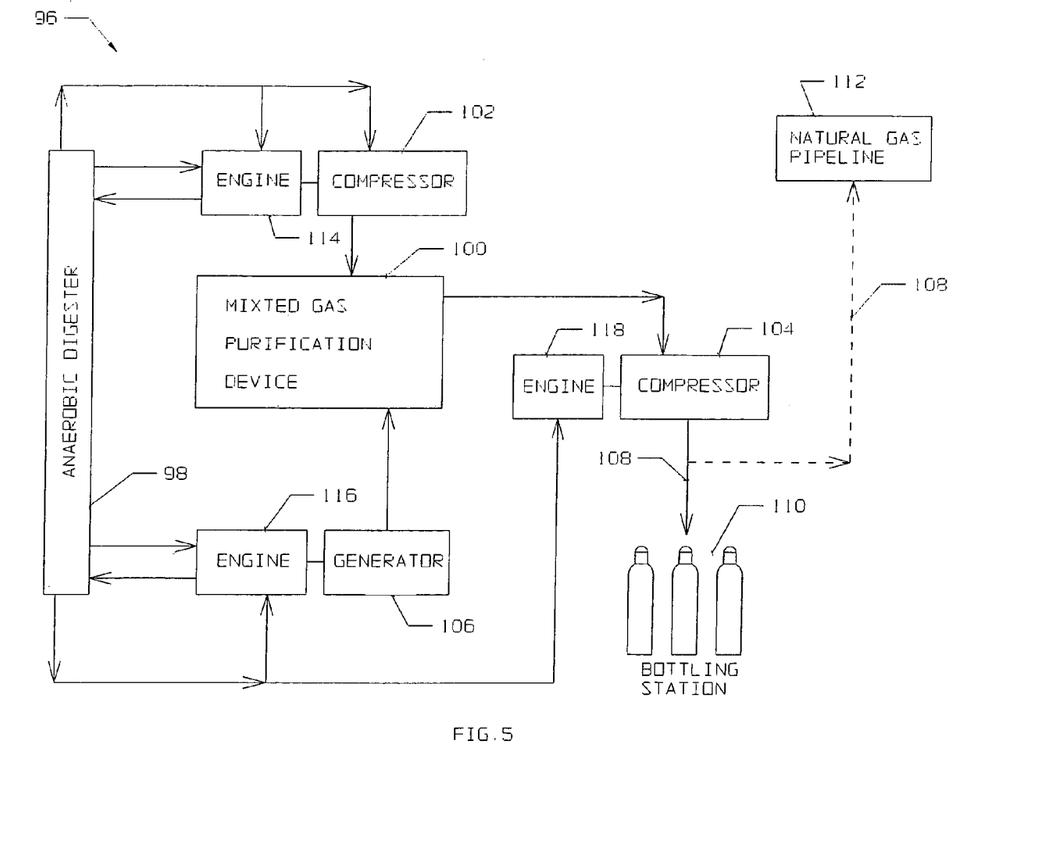
FIG. 5 is a process flow schematic of a most preferred embodiment of the methane generation system of the present invention.

Referring now to FIG. 5, a second most preferred embodiment of the present inventive system is shown and generally designated by reference numeral 96. In this second most preferred embodiment, system 96 comprises:

1) an anaerobic digester 98;
2) a mixed gas purification device 100;
3) first and second mixed gas-driven compressors 102, 104, in fluid communication with the anaerobic digester 98 and in further fluid communication with the mixed gas purification device 100;
4) a mixed gas-driven generator 106 in fluid communication with the anaerobic digester 98 and in electrical communication with the mixed gas purification device 100; and
5) means 108 for directing the methane product stream exiting the second compressor 104 to a bottling station 110 and/or to a natural gas pipeline 112.

In operation, mixed gases from digester 98 are initially directed to gas-driven engines 114, 116, which power the first compressor 102 and the generator 106, respectively. Once the first compressor 102 and the generator 106 are operational, they are brought online along with the mixed gas purification device 100. Mixed gases from digester 98 are then directed to gas-driven engine 118, for powering the second compressor 104. Once sufficient methane gas flow rates (i.e., 25 to 30% of rated output) are achieved, the second compressor 104 is brought online. As noted above, the methane gas may be directed to e.g., a bottling station 110 and/or to a natural gas pipeline 112.

The process employed by the methane and/or high purity hydrogen generation systems 10, 68, 96 of the present invention may be summarized as set forth below:

1) anaerobically digesting organic materials by the action of bacteria and/or enzymes contained therein to produce a mixed gas stream containing, among other things, methane, carbon dioxide and trace impurities such as hydrogen sulfide, nitrogen and oxygen;
2) optionally, directing at least a portion of the mixed gas stream to means for removing at least a portion of the hydrogen sulfide gas contained therein;
3) directing portions of the optionally condensed, mixed gas stream to gas-driven engines that power:
   a. a generator, wherein the generator produces electrical energy for powering a hydrogen generation and removal system and/or a mixed gas purification device;
   b. a first compressor;
   c. one or more mixed gas-fired reforming furnaces (during startup and operation);
   d. one or more steam boilers (during startup and operation); and
   e. optionally, a second compressor, wherein the mixed gas stream serves to fuel the gas-driven engines,
4) directing remaining portions of the optionally desulfurized, mixed gas stream to the first compressor for compressing or pressurizing the gas stream; and
5) directing the compressed, optionally desulfurized, mixed gas stream to a mixed gas purification device for removing impurities and/or to a hydrogen generation and removal system comprising (a) means for generating a hydrogen-rich gas from the mixed gas stream, and (b) means for selectively removing hydrogen from the hydrogen-rich gas to produce a high purity hydrogen product stream,
   wherein, when the compressed, optionally condensed, mixed gas stream is directed to the mixed gas purification device for removing impurities, the resulting purified, compressed, optionally condensed, mixed gas stream is then directed to the second compressor for further compressing the gas stream prior to directing the gas stream into e.g., a natural gas pipeline and/or cylinders or tube trailers for storage and/or shipment, and
   wherein, when the compressed, optionally condensed, mixed gas stream is directed to the hydrogen generation and removal system, the resulting high purity hydrogen product stream is directed to one or more hydrogen fueled devices (e.g., a hydrogen electrical generator) and/or to the second compressor for further compressing the high purity hydrogen product stream prior to directing the product stream into e.g., cylinders or tube trailers for storage and/or shipment.

Although this invention has been shown and described with respect to detailed embodiments thereof, it will be apparent to those skilled in the art that various changes in form and detail thereof may be made without departing from the spirit and scope of the invention. For example, biogas or mixed gases may also be produced in a composting facility, or the like, while motorized compressors (e.g., motorized diaphragm-style compressors) may be used instead of compressors operated by gas-driven engines. For the latter embodiment, the generator 20, 78, 106 would supply electricity to the motorized compressor(s), as well as, the hydrogen generation and removal system 32, 72 and/or the mixed gas purification device 34, 100.

The invention claimed is:

1. A self-contained and streamlined methane and high purity hydrogen generation system, comprising:
   (a) an anaerobic digester for anaerobically digesting organic materials by the action of bacteria and/or enzymes contained therein to produce a mixed gas stream containing methane, carbon dioxide and trace impurities including hydrogen sulfide, nitrogen and oxygen;
   (b) at least one compressor in fluid communication with the anaerobic digester and in further fluid communication with a hydrogen generation and removal system and a mixed gas purification device;
   (c) at least one mixed gas-driven generator in fluid communication with the anaerobic digester and in electrical communication with the hydrogen generation and removal system and the mixed gas purification device, and optionally, in further electrical communication with the compressor(s); and
   (d) (i) the mixed gas purification device, which serves to remove hydrogen sulfide and/or carbon dioxide from the mixed gas stream to produce a methane product stream, wherein the mixed gas purification device is in fluid communication with the compressor and is in electrical communication with the generator; and
   (ii) the hydrogen generation and removal system, which comprises means for generating a hydrogen-rich gas from the compressed, mixed gas stream, and means for selectively removing hydrogen from the hydrogen-rich gas to produce a high purity hydrogen product stream, wherein the hydrogen generation and removal system has an operating pressure, and is in fluid communication with the compressor and is in electrical communication with the generator.

2. The self-contained and streamlined methane and high purity hydrogen generation system of claim 1, wherein the system is dedicated to the production of methane gas and produces from about 40 to about 2,400 standard liters per minute of methane gas at pressures ranging from about 1.82 to about 2.86 megapascals, wherein the methane gas has a purity level of greater than 90%.

3. The self-contained and streamlined methane and high purity hydrogen generation system of claim 1, wherein the system is dedicated to the production of hydrogen gas and produces from about 40 to about 2,400 standard liters per minute of hydrogen gas at pressures ranging from about 100 to about 450 kilopascals, wherein the hydrogen gas has a purity level of greater than 99.99999%.

4. The self-contained and streamlined methane and high purity hydrogen generation system of claim 1, wherein the system produces both methane gas and high purity hydrogen gas.

5. The self-contained and streamlined methane and high purity hydrogen generation system of claim 2 or 4, wherein the at least one compressor compresses the mixed gas stream from the digester to a pressure exceeding the operating pressure of the mixed gas purification device.

6. The self-contained and streamlined methane and high purity hydrogen generation system of claim 3 or 4, wherein the at least one compressor compresses the mixed gas stream from the digester to a pressure exceeding the operating pressure of the hydrogen generation and removal system.

7. The self-contained and streamlined methane and high purity hydrogen generation system of claim 6, wherein the at least one compressor compresses the mixed gas stream from the digester to a pressure of greater than or equal to 2.17 megapascals.

8. The self-contained and streamlined methane and high purity hydrogen generation system of claim 7, wherein the at least one compressor compresses the mixed gas stream to a pressure of greater than or equal to 2.86 megapascals.

9. The self-contained and streamlined methane and high purity hydrogen generation system of claim 2 or 4, wherein the mixed gas purification device comprises an absorbent selected from the group of activated charcoal, zinc oxide and mixtures thereof, which serves to remove hydrogen sulfide from the compressed, mixed gas stream.

10. The self-contained and streamlined methane and high purity hydrogen generation system of claim 2 or 4, wherein the mixed gas purification device comprises at least one selective membrane or film, which serves to remove carbon dioxide from the compressed, mixed gas stream, wherein the selective membrane or film is selected from the group of cellulose acetate, polysulfone and polyimide membranes and films and membranes made from fluorinated polymers.

11. The self-contained and streamlined methane and high purity hydrogen generation system of claim 3 or 4, wherein the means for generating a hydrogen-rich gas from the compressed, mixed gas stream comprises a steam reformer and a high temperature shift reactor.

12. The self-contained and streamlined methane and high purity hydrogen generation system of claim 11, wherein the means for generating a hydrogen-rich gas further comprises means for removing hydrogen sulfide from the compressed, mixed gas stream entering the hydrogen generation and removal system.

13. The self-contained and streamlined methane and high purity hydrogen generation system of claim 3 or 4, wherein the means for selectively removing hydrogen from the hydrogen-rich gas comprises one or more hydrogen-permeable membranes.

14. The self-contained and streamlined methane and high purity hydrogen generation system of claim 3 or 4, wherein the hydrogen generation and removal system comprises a steam reformer and a high temperature shift/membrane reactor, wherein the high temperature shift/membrane reactor comprises, in one unit, a reactor that generates hydrogen and at least one hydrogen-permeable membrane that extracts hydrogen.

15. The self-contained and streamlined methane and high purity hydrogen generation system of claim 14, wherein the high temperature shift/membrane reactor comprises: a chamber; an inlet port for introducing the compressed, mixed gas stream into the chamber; a plurality of hydrogen-permeable membranes in the form of tubes having an outer surface in fluid communication with the compressed, mixed gas stream, and an inner surface in fluid communication with a hydrogen product stream that passes through the tubes housed within the chamber; a catalyst located within the chamber for facilitating an exothermic water-gas shift reaction; a first outlet port for removing the hydrogen product stream; a second outlet port for removing a waste gas stream; and optionally, cooling means for withdrawing thermal energy from the chamber.

16. A self-contained and streamlined methane and/or high purity hydrogen generation system, which comprises:
(a) an anaerobic digester for anaerobically digesting organic materials by the action of bacteria and/or enzymes contained therein to produce a mixed gas stream containing methane, carbon dioxide and trace impurities including hydrogen sulfide, nitrogen and oxygen, wherein the mixed gas stream may also contain small quantities of water;
(b) first and second mixed gas-driven compressors in fluid communication with the anaerobic digester and in further fluid communication with a hydrogen generation and removal system having an operating pressure, wherein the first mixed gas-driven compressor compresses the mixed gas stream from the digester to a pressure exceeding the operating pressure of the hydrogen generation and removal system, and wherein the second mixed gas-driven compressor compresses a high purity hydrogen product stream from the hydrogen generation and removal system to a pressure of greater than or equal to 20.8 megapascals;
(c) the hydrogen generation and removal system, which comprises a steam reformer and a high temperature shift/membrane reactor, wherein the hydrogen generation and removal system generates a hydrogen-rich gas from the compressed, mixed gas stream exiting the first mixed gas-driven compressor, and selectively removes hydrogen from the generated hydrogen-rich gas to produce a high purity hydrogen product stream;
(d) a mixed gas-driven generator in fluid communication with the anaerobic digester and in electrical communication with the hydrogen generation and removal system for powering same;
(e) optionally, a condenser in fluid communication with the anaerobic digester for removing at least a portion of any water contained in the mixed gas stream produced by the digester;
(f) means for directing the high purity hydrogen product stream exiting the hydrogen generation and removal system to low-pressure hydrogen fueled devices; and
(g) means for directing the high purity hydrogen product stream exiting the second compressor to one or more high pressure storage receptacles.

17. A self-contained and streamlined methane and/or high purity hydrogen generation system, which comprises:
(a) an anaerobic digester for anaerobically digesting organic materials by the action of bacteria and/or enzymes contained therein to produce a mixed gas stream containing methane, carbon dioxide and trace impurities including hydrogen sulfide, nitrogen and oxygen, wherein the mixed gas stream may also contain small quantities of water;
(b) first and second mixed gas-driven compressors in fluid communication with the anaerobic digester and in further fluid communication with a mixed gas purification device having an operating pressure, wherein the first mixed gas-driven compressor compresses the mixed gas stream from the digester to a pressure exceeding the operating pressure of the mixed gas purification device, and wherein the second mixed gas-driven compressor compresses a methane product stream from the mixed gas purification device to a pressure of greater than or equal to 20.8 megapascals;
(c) the mixed gas purification device, which serves to remove hydrogen sulfide and/or carbon dioxide from the mixed gas stream exiting the first mixed gas-driven compressor to produce a methane gas product stream;
(d) a mixed gas-driven generator in fluid communication with the anaerobic digester and in electrical communication with the mixed gas purification device for powering same;

(e) optionally, a condenser in fluid communication with the anaerobic digester for removing at least a portion of any water contained in the mixed gas stream produced by the digester; and
(f) means for directing the methane gas product stream exiting the second compressor to a bottling station and/or to a natural gas pipeline.

18. A self-contained and streamlined methane generation system, comprising:
   (a) an anaerobic digester for anaerobically digesting organic materials by the action of bacteria and/or enzymes contained therein to produce a mixed gas stream containing methane, carbon dioxide and trace impurities including hydrogen sulfide, nitrogen and oxygen;
   (b) at least one compressor in fluid communication with the anaerobic digester and in further fluid communication with a mixed gas purification device;
   (c) at least one mixed gas-driven generator in fluid communication with the anaerobic digester and in electrical communication with the mixed gas purification device, and optionally, in further electrical communication with the compressor(s); and (d) the mixed gas purification device, which serves to remove hydrogen sulfide and/or carbon dioxide from the mixed gas stream to produce a methane product stream, wherein the mixed gas purification device is in fluid communication with the compressor and is in electrical communication with the generator.

19. A self-contained and streamlined high purity hydrogen generation system, comprising:
   (a) an anaerobic digester for anaerobically digesting organic materials by the action of bacteria and/or enzymes contained therein to produce a mixed gas stream containing methane, carbon dioxide and trace impurities including hydrogen sulfide, nitrogen and oxygen;
   (b) at least one compressor in fluid communication with the anaerobic digester and in further fluid communication with a hydrogen generation and removal system;
   (c) at least one mixed gas-driven generator in fluid communication with the anaerobic digester and in electrical communication with the hydrogen generation and removal system, and optionally, in further electrical communication with the compressor(s); and
   (d) the hydrogen generation and removal system, which comprises means for generating a hydrogen-rich gas from the compressed, mixed gas stream, and means for selectively removing hydrogen from the hydrogen-rich gas to produce a high purity hydrogen product stream, wherein the hydrogen generation and removal system has an operating pressure, and is in fluid communication with the compressor and is in electrical communication with the generator.

* * * * *